(12) United States Patent
Macoviak

(10) Patent No.: US 6,893,459 B1
(45) Date of Patent: May 17, 2005

(54) HEART VALVE ANNULUS DEVICE AND METHOD OF USING SAME

(75) Inventor: John A. Macoviak, La Jolla, CA (US)

(73) Assignee: Ample Medical, Inc., Foster City, CA (US)

( * ) Notice: Subject to any disclaimer, the term of this patent is extended or adjusted under 35 U.S.C. 154(b) by 150 days.

(21) Appl. No.: 09/666,617

(22) Filed: Sep. 20, 2000

(51) Int. Cl.⁷ .............................................. A61F 2/24
(52) U.S. Cl. .................................. 623/2.11; 623/2.38
(58) Field of Search .......................... 623/2.38, 2.11, 623/2.12, 2.14, 2.17, 2.18

(56) References Cited

U.S. PATENT DOCUMENTS

| | | |
|---|---|---|
| 2,522,038 A | 9/1950 | Houghton |
| 3,143,742 A * | 8/1964 | Cromie .................... 623/2.38 |
| 3,686,740 A * | 8/1972 | Shiley ........................ 29/439 |
| 4,655,218 A | 4/1987 | Kulik et al. |
| 4,788,966 A | 12/1988 | Yoon |
| 4,850,354 A | 7/1989 | McGurk-Burleson et al. |
| 4,865,600 A | 9/1989 | Carpentier et al. |
| 4,889,118 A | 12/1989 | Schwiegerling |
| 5,147,379 A | 9/1992 | Sabbaghian et al. |
| 5,217,474 A | 6/1993 | Zacca et al. |
| 5,236,450 A | 8/1993 | Scott |
| 5,476,510 A | 12/1995 | Eberhardt et al. |
| 5,545,214 A | 8/1996 | Stevens |
| 5,586,991 A | 12/1996 | Yoon |
| 5,601,583 A | 2/1997 | Donahue et al. |
| 5,669,918 A | 9/1997 | Balazs et al. |
| 5,682,906 A | 11/1997 | Sterman et al. |
| 5,695,515 A | 12/1997 | Orejola |
| 5,697,382 A | 12/1997 | Love et al. |
| 5,713,849 A | 2/1998 | Bosma et al. |
| 5,716,370 A | 2/1998 | Williamson, IV et al. |
| 5,716,402 A | 2/1998 | Reif |
| 5,741,287 A | 4/1998 | Alden et al. |
| 5,759,185 A | 6/1998 | Grinberg |
| 5,766,200 A | 6/1998 | Mazurek et al. |
| 5,776,156 A | 7/1998 | Shikhman |
| 5,779,721 A | 7/1998 | Nash |
| 5,782,795 A | 7/1998 | Bays |
| 5,814,097 A | 9/1998 | Sterman et al. |
| 6,287,339 B1 * | 9/2001 | Vazquez et al. ............. 623/2.4 |
| 6,312,465 B1 * | 11/2001 | Griffin et al. .............. 623/2.38 |

* cited by examiner

Primary Examiner—Alvin Stewart
(74) Attorney, Agent, or Firm—Ryan Kromholz & Manion, S.C.

(57) ABSTRACT

A method of implanting a universal heart valve prosthetic anchor device for receipt of a mating occluder. The anchor device includes a pair of rings axially shiftable from a retracted to a deployed position. The anchor device further formed with a plurality of flexible retaining elements received within the anchor rings and which are capable of laterally downwardly outward movement upon deployment of the rings. The deployment tool includes an elongated tubular housing mounted at its distal end with radially outwardly diverging tines for reversible engagement with the anchoring rings. A wire is telescoped through the tines for actuation of the fork thereby causing deployment of the anchoring rings. Once placed at the desired location within the heart muscle, the deployment tool is actuated causing the anchor device to shift axially thereby causing the retainers to deploy outwardly and upwardly to secure the valve anchor in place at the heart valve annulus shelf.

6 Claims, 11 Drawing Sheets

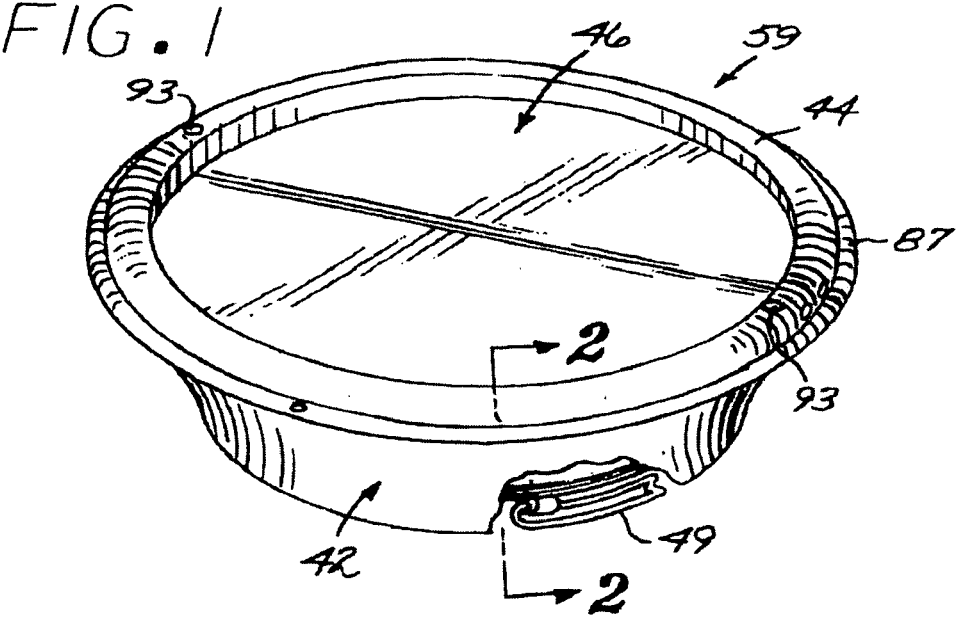
FIG. 1
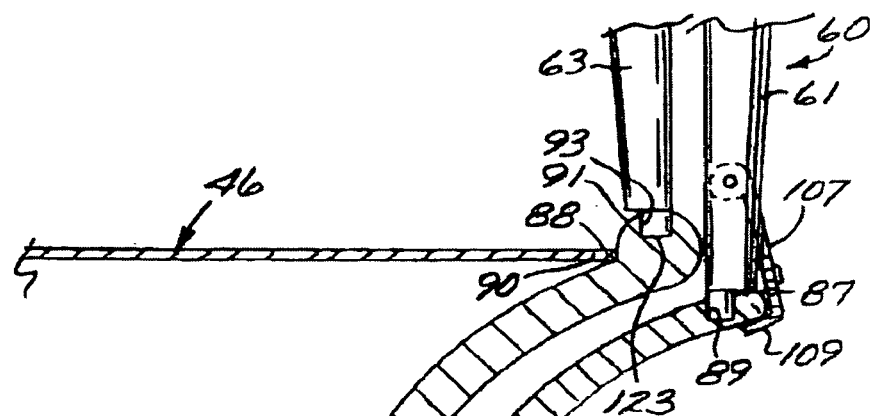
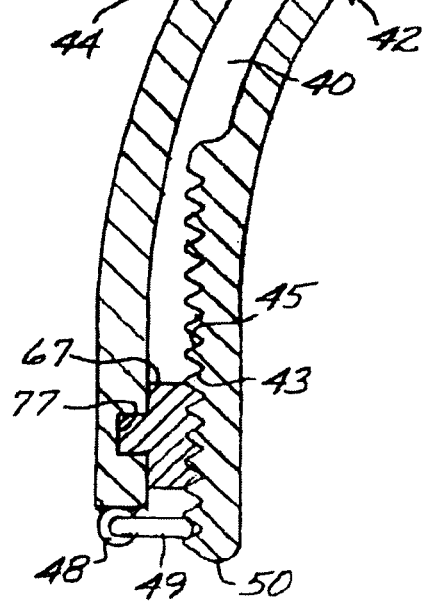
FIG. 2

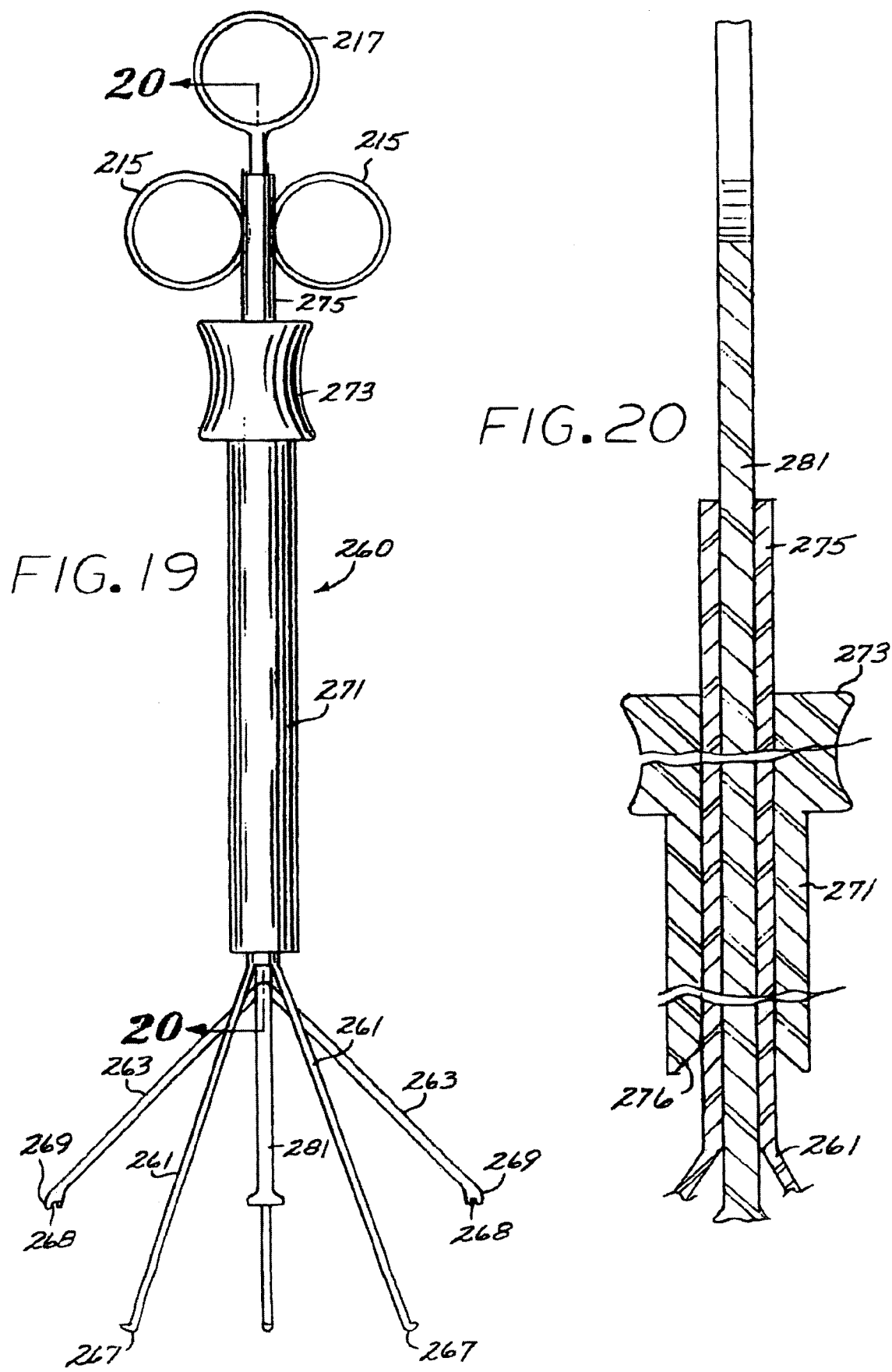

HEART VALVE ANNULUS DEVICE AND METHOD OF USING SAME

BACKGROUND OF THE INVENTION

1. Field of the Invention

The present invention relates to a prosthetic heart valve anchor and a minimally invasive method for implantation.

2. Description of the Prior Art

It has been estimated that up to 20% of all cardiac surgeries are directly related to valve replacement or implantation of artificial valves. It is well known that a variety of medical conditions and diseases may cause damage to the heart valve which ultimately necessitates valve replacement. Certain diseases such as rheumatic fever can cause the valve orifice to shrink or pull apart. If these defects are not corrected, prolonged valvular stenosis or insufficiency may cause damage to the heart muscle and may even require complete valve replacement. Other indications, including congenital anomalies and myocardial infarction, may necessitate total valve replacement as well.

When complete valve replacement is necessary, the surgeon may choose from two types of prosthetic valves, mechanical or tissue valves. Mechanical valves are generally made from some type of rigid metal or hard plastic. They have been known to be formed from titanium coated with a pyrolytic carbon with polymer and biocompatible cloth covered sewing rings. Most of these currently available mechanical valves are either of a pivoting bi-leaflet or tilting mono-leaflet design. However, more flexible or elastic valves may be achieved using synthetic polymers which simulate a biological tissue valve.

Tissue valves, in contrast, consist of chemically preserved or cryopreserved animal tissue including human homografts and xenografts usually extracted from a pig or cow and typically mounted on a supporting frame known as a "valve stent". The valve stent itself is constructed from a metal and polymer material and covered with a biocompatible cloth material. A sewing ring is then used to tether the valve to the annulus. The sewing ring is typically a tubular synthetic structure which is designed to allow passage of the suture through the sewing ring in order to tether the valve. The sewing ring may be comprised of a biocompatible cloth which covers a silicone sewing ring and further having three valve stent commissure posts which project upward from the cloth and which serve to hold the three tissue leaflets of the valve in proper placement. Additionally, the valve stent provides a structural integrity which enables the surgeon to insert and mount the valve into the heart and suture it into place. These tissue valves are inherently advantageous because they are less likely to cause thrombosis, thereby reducing the necessity of having the patient treated with anticoagulants. However the failure rate of these bioprosthetic valves is at 15% by fifteen years after surgery, and therefore these tend to require periodic replacement.

While heart valve implants have become widely accepted in the medical field, this procedure is still extremely costly. The medical personnel necessary for the procedure must comprise a skilled surgeon, perfusionist, anesthesiologist and a full operating room staff, as well as equipment which include a sophisticated heart/lung bypass machine. In addition to the expensive personnel, valve implant surgery requires extensive operating time which is both costly and subjects the patient to a greater health risk the longer he is on a bypass machine and under anesthesia.

It is the generally accepted practice in the medical field to implant prosthetic heart valve devices by means of surgical suturing of the valve into the heart. Valve designs currently on the market make the suturing technique advantageous because they permit direct securing of the valve with precise and easy visualization of the suture line. While there are a variety of advantages to this standard means of sewing the heart valve into orthotopic or heterotopic positions, there still remain a vast number of disadvantages which make an alternative means desirable to find. The sewing ring used to suture the valve into the patient's heart occupies a significant annulus area and therefore effectively reduces the amount of valve orifice area. Furthermore, suture placement itself can be a tedious process which often demands a significant portion of the overall operation time. This is especially true in the case of younger or small patients as well as those patients who have undergone repeat procedures. Based on the need to reduce the overall length of time a patient undergoes surgery, one can appreciate that reduced suturing time or removal of the suturing process altogether is highly advantageous.

In addition, the accepted practice of hand suturing traditional prosthetic heart valves into place requires large open access to the chest cavity to enable the surgeon to precisely suture the valve into the heart muscle. Access is usually made through the open chest and a longitudinal incision in the ascending aorta is typically utilized for handheld instruments utilized for both valve placement and suturing. Accurate placement and orientation of the valve within the heart is a difficult and high risk aspect of this procedure which may be minimized by enlarging the chest openings, giving the surgeon better access and increasing the prospect that the valve will be placed successfully. For most cardiovascular surgeries, the need for precise suturing for securement of the heart valve prosthetic has been difficult to improve upon.

Therefore, while adequate access to the chest cavity has been considered necessary during heart valve replacement, it is an extremely traumatic event for the patient and subjects them to a higher risk of infection. Thus it can be appreciated that the need exists for a heart valve prosthetic that is subject to placement using minimally invasive surgical techniques.

Additionally, suturing the prosthesis valve into the heart muscle creates a subsequent problem for the patient due to the fact that the valve itself is bulky, and when sutured into place, the suturing process necessarily reduces the cross section of the flow path through the valve body. Such a flow restriction may adversely affect blood flow which may increase the transvalvular pressure gradients of the heart thereby requiring it to work harder to pump the same volume of blood. For a patient already experiencing heart stress, the increased pressure on the heart is clearly undesirable.

In addition to the restriction within the heart valve itself, narrowing of the valve structure is often brought on by the surgeon pulling the sutures as snugly as possible during placement of the prosthetic. The more snugly the valve fits the better. However, the result is that the tissue becomes constricted at the site of the implant. Another problem with the suturing technique is a tendency to constrict the heart annulus. Constrictions occur when sutures draw the heart annulus upwardly toward the valve sewing ring thereby drawing it partially into the annular opening of such sewing ring. Other problems associated with suturing of the valve prosthetic occur when the suture is placed too deeply into the muscle wall. When the suture extends deep into the muscle wall, the suture can catch the back wall of a contiguous structure thereby causing damage to that tissue or otherwise injuring the cardio-conduction system which may result in conduction abnormalities. Similarly, the relationship between the leaflets and the cloth covering of the stent in biological tissue valves promotes pannus fibrosing tissue depositing, which eventually creeps inward from the periphery of the valve.

Similarly, sutures securing a valve in place may cause the formation of blood clots due to the presence of additional foreign objects in the body. The danger caused by these blood clots can be severe if a clot breaks away and enters the patient's blood stream, thereby causing a major health problem such as a heart attack or stroke. Additionally, the very nature of sutures creates problems because when the surgeon stitches the sew cuff in place, he or she knots and cuts the thread leaving raw edges somewhat exposed to the patient's blood stream. These raw edges create another area of potential blood clot formation and infection. Due to the location of these potential blood clots, a formed clot may even extend into the valve itself thus trapping it open or shut and generally causing overall valve malfunctions. It has been the general practice to administer an anti-coagulant such as heparin or warfarin to post-surgical patients in an attempt to reduce this potential for blood clotting. However, it can be appreciated that a valve prosthetic, which itself does not produce blood clots, is a safer and overall better alternative than administration of a blood thinning drug. It has also been observed that the presence of foreign materials in the body, such as sutures and staples, increases the potential for bacterial infection at that site. Therefore the benefit of reducing the suture requirement becomes apparent.

While there is an obvious need to provide a sutureless heart valve prosthetic, such a valve must also still fit snugly and securely in the heart annulus. Without a secure fit between the prosthetic and the tissue, leaks may develop between the valve anchor and heart annulus thereby allowing blood to bypass the valve. Such a situation may be disastrous. Therefore, while a need exists to find a viable alternative to suturing, the valve anchor must securely attach to the heart muscle without exhibiting leakage.

Many efforts have been made over the years to provide a satisfactory anchoring ring for a prosthetic valve and a tool for placement thereof. One such effort focused on the problems associated with suturing. A cuff was proposed having an exterior fabric skirt connected therewith to be stapled to the native annulus to anchor the cuff in position. A rather elaborate tool was proposed for implanting the cuff and stapling the skirt to the annulus. Devices of this type are shown in U.S. Pat. No. 5,716,370 to Williamson et al. Such devices, while offering interesting solutions, are relatively complex and have not gained general acceptance in the field. Furthermore, the use of staples instead of sutures has been known to exhibit similar scarring and tension effects.

Another effort to create a secure valve holder which is also capable of reducing potential damage to the heart tissue was proposed as an assembly including a heart valve having a plurality of radially inwardly deflectable supports and a holder having inner and outer members for suture attachment and to ensure a counterbalancing of the suture tension. A device such as this is disclosed in U.S. Pat. No. 4,865,600 to Carpentier et al. While relatively effective in solving certain problems, such an assembly is fairly large and cumbersome as well as being mechanically complex.

Other devices for implanting a heart valve have been proposed which include a fork shaped tool having projecting tines which are flexibly mounted and formed on their distal ends with hooks which may be spread radially outwardly to releaseably hook into the interior of the cuff and be biased in position by a removable biasing spring which may be removed after implantation. A device of this type is shown in U.S. Pat. No. 5,236,450 to Scott. A device of this nature, while effective to grip a conventional cuff, does not provide for mechanical anchoring of the cuff to the annulus or provide for an arrangement for deployment of a mechanically anchoring device.

Therefore, it is clear that the need exists for a novel heart valve placement system which permits the surgeon to quickly, easily and securely implant the heart valve into the patient with minimal resulting trauma to the patient and yet which is simple to construct and use and which achieves a high level of success.

SUMMARY OF THE INVENTION

The prosthetic valve anchor of the present invention may be implanted with mechanical retainers anchoring it facilitate the anchoring procedure. In some embodiments, separate suture eyes may be provided so that, once mechanically anchored in place, a selected number of supplemental sutures may be made to further facilitate anchoring. The anchor ring may incorporate a mounting arrangement for removably mounting an occluder thereto. This mounting arrangement, in some instances, is universal in that it will accept occluders manufactured by different manufacturers such that the single anchor ring will anchor different models of occluders. The anchor mechanism may be of the screw type, a rail fastener, a bayonet style engagement or any other type of mounting device as known to those skilled in the art. In one embodiment, the occluder may be removed with the anchor left in place. The anchor then cleaned up and a replacement occluder inserted without removal of the anchor.

In another embodiment, the prosthetic valve anchor may be formed by a ring device to be positioned in the opening of the heart annulus and having mechanically deployable mechanical retainer elements projectable radially outwardly to engage under the shelf of the heart annulus to anchor it in position. In one embodiment, the anchoring elements are formed integral with the ring and the ring is compressible axially to deploy such elements radially outwardly. In another embodiment, the anchor device includes a pair of interfitting rings which are rotatable relative to one another and mount therebetween a retaining mechanism operable upon rotation of such rings relative to one another to project such retainers radially outwardly under such shelf.

The deployment tool includes an elongated tube mounting at its distal extremities with radially outwardly diverging tines for releaseable engagement on one location with the anchoring ring or rings and having a wire telescoped therethrough and mounting at its distal end an actuating fork having tines for engagement on a second location of such anchoring ring or rings. The wire is shiftable relative to the legs so that the tines may be manipulated relative to the tube to thereby shift the portions of the anchoring ring or rings relative to one another to deploy the retainers radially outwardly under the annulus shelf.

The method of the present invention involves accessing the patient's heart annulus and securing the anchor device to a deployment tool to introduce it to the heart annulus and deploy the retainer elements.

As can be seen, the heart valve anchor of the present invention takes advantage of mechanical retainers to minimize the time consuming process of suturing the valve anchor into place, thereby greatly reducing the overall time necessary to complete the surgical procedure. Such anchor offers the advantage that it can be implanted separate and independent of the occluder thus enhancing its maneuverability and providing ready visual and physical access thereto for ease of placement and mounting of the occluder. Similarly, the heart valve anchor of the present invention solves a variety of problems associated with suture techniques including reduced valve size, pannus creep, and the in-growth of fibrosis which can cause valve failure. Furthermore, this procedure may be utilized without subjecting the patient to open chest surgery which reduces the incidence of infection to the patient in addition to the obvious reduction in the overall trauma experienced by the body.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 1 is a perspective view, partially broken away, of a prosthetic heart valve anchor device embodying the present invention;

FIG. 2 is a sectional view, in enlarged scale, taken the lines 2—2 of FIG. 1 and depicting a deployment tool engaged with such anchor device;

FIG. 19 is a side view of the tool utilized to deploy the anchor device shown in FIGS. 16 and 17;

FIG. 20 is a partial broken longitudinal sectional view, in enlarged scale, taken along line 20—20 of FIG. 19;

DETAILED DESCRIPTION OF A PREFERRED EMBODIMENT

Figure 10:
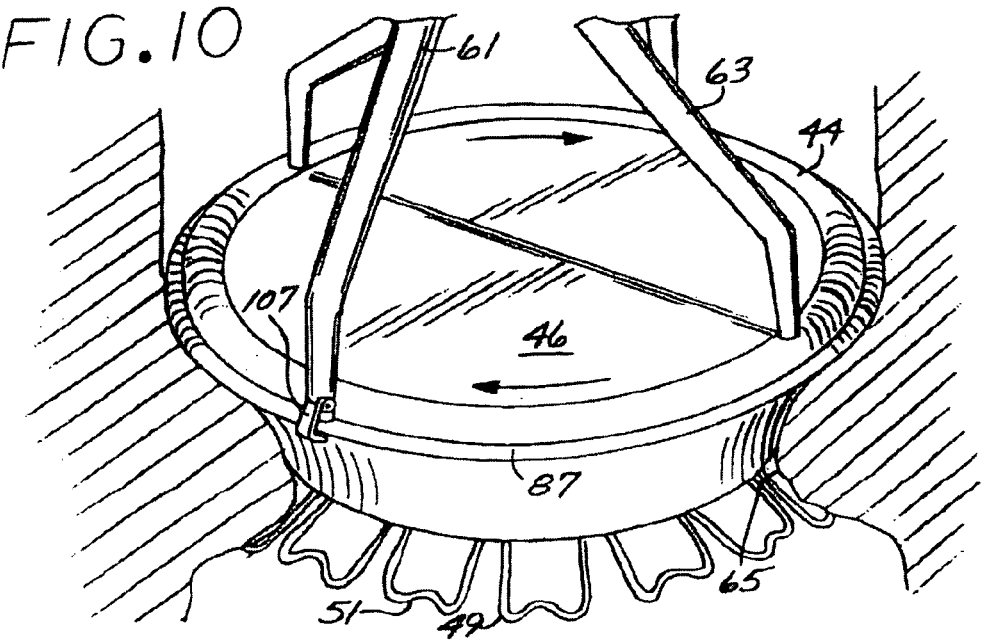
FIG. 10 is a view similar to FIG. 9 but showing the retaining device as being deployed.

The prosthetic heart valve anchor apparatus of the prevent invention includes, generally, outer and inner elongated concentric rings 42 and 44 with the top end of the inner ring being closed at its proximal end by a pair of hinged oblators 46. Referring to FIG. 2, the rings 42 and 44 are spaced radially apart to form therebetween an annulus 40 into which is received at the lower extremity a plurality of radially outwardly biased conformable retainer fingers 49. Such fingers are mounted at their radially inner extremities to the bottom end of the inner ring 44 by means of anchor sleeves 48 and selectively retained in their retracted position by the bottom extremity 50 of the inner ring. With continued reference to FIG. 2, the inner and outer rings are formed with respective screw threads 43 and 45. Laterally spaced apart legs 61 of a deployment tool, generally designated 60, are engageable with the top end of the outer ring 42 and laterally spaced tines of a fork 63 are engageable with the top end of the inner ring 44. Such legs and fork are rotated relative to one another to rotate such rings relative to one another to shift them longitudinally on their screw threads to shift the lower extremity 50 of such outer ring upwardly as such extremity 50 clears the free extremities of the retainer fingers 49 so they flex radially outwardly to the positions shown in FIG. 3 to project outwardly under the shelf of the annulus 65 (FIG. 10).

Figure 3:
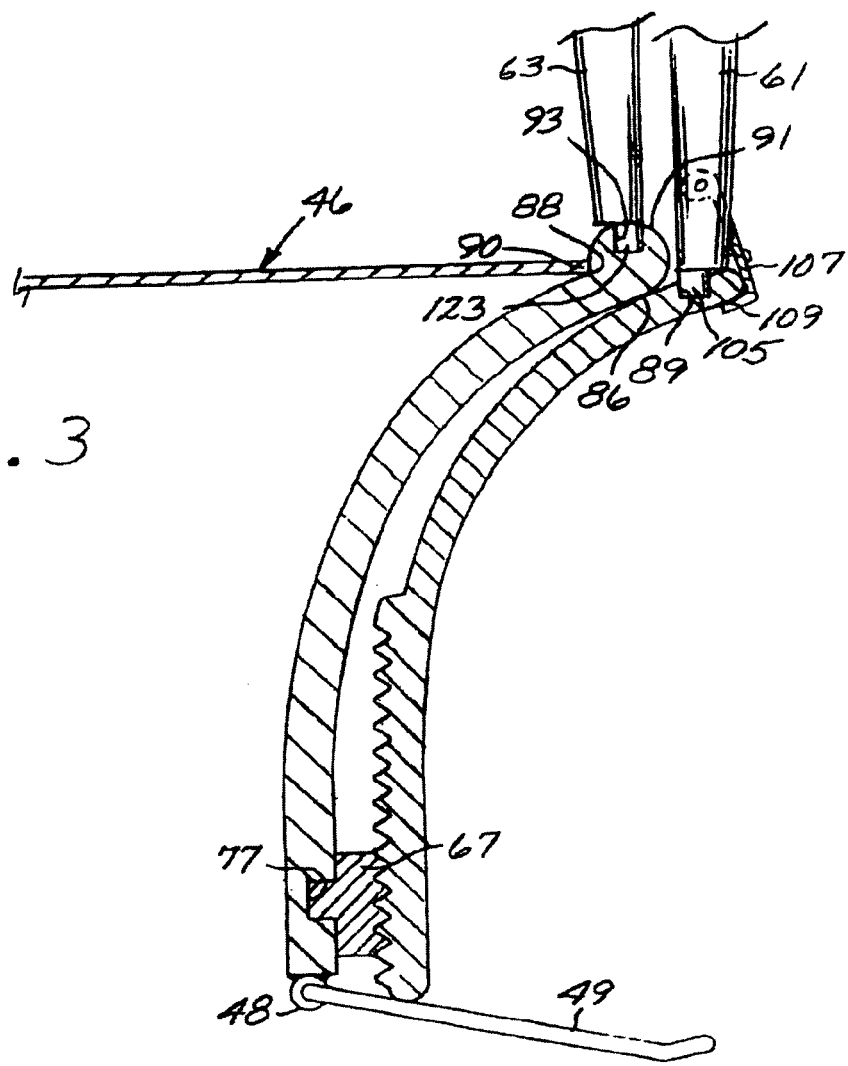
FIG. 3 is a sectional view, similar to FIG. 2, but showing rings in such anchor device shifted relative to one another.

The rings 42 and 44 are constructed of a rigid or semi-rigid material such as titanium or plastic and then coated with a biocompatible substance such as pyrolytic carbon. In the preferred embodiment, the rings 42 and 44 are somewhat in the shape of inverted bells to flare longitudinally upwardly and radially outwardly as viewed in FIGS. 1 and 2. The outer ring 42 is formed in its distal extremity (FIG. 2) with the internal threads 45 to engage with external threads 43 formed on the wall of an actuator or coupler, generally designated 67, mounted to a groove 77 in the exterior wall of the interior ring 44. The upper extremity of the outer ring 42 is formed with a radially outwardly curved connector flange 87 formed with an upwardly opening blind drive bore 89. The inner ring 44 flares outwardly to form a flare disposed above the proximal flare in the exterior ring 42 and in the path thereof to form a stop 86 (FIG. 3) to be abutted by the top side of the exterior ring flare to thus limit proximal travel of such exterior ring 42 relative to the interior ring 44. The inner ring flare is formed on its top side with a circular bead 91 having a pair of diametrically oppositely disposed, upwardly opening drive bores 93 formed therein to be engaged by respective drive pins 123 formed at the end of the respective tines 63. Such bead 91 is formed radially inwardly with a universal mounting socket 88 opening upwardly for receipt of a frame 90 mounting the occluders 46 (FIG. 3). It can be appreciated that the actuator 67 could take a variety of forms designed to translate movement, such as a pawl and ratchet mechanism actuable by reciprocation of such rings to progressively advance the relative rotation thereof.

It is understood by those skilled in the art that the shape of the rings of the anchor device may take a variety of forms not merely that of a bell. One could appreciate that the anchor may be formed in the shape of a pair of concentric rings which are deformable upon actuation. Additionally, the rings may even be formed in the shape of an hourglass with a flexible property for easy insertion at the annulus shelf. It can also be appreciated that the diameter and height of the anchor of the present invention cannot be limited. Since heart valve replacement procedures are conducted on infants, children and adults alike, there is a limitless variation of heart valve sizes which must be taken into consideration, thus the size of the apparatus cannot be limiting.

Figure 5:
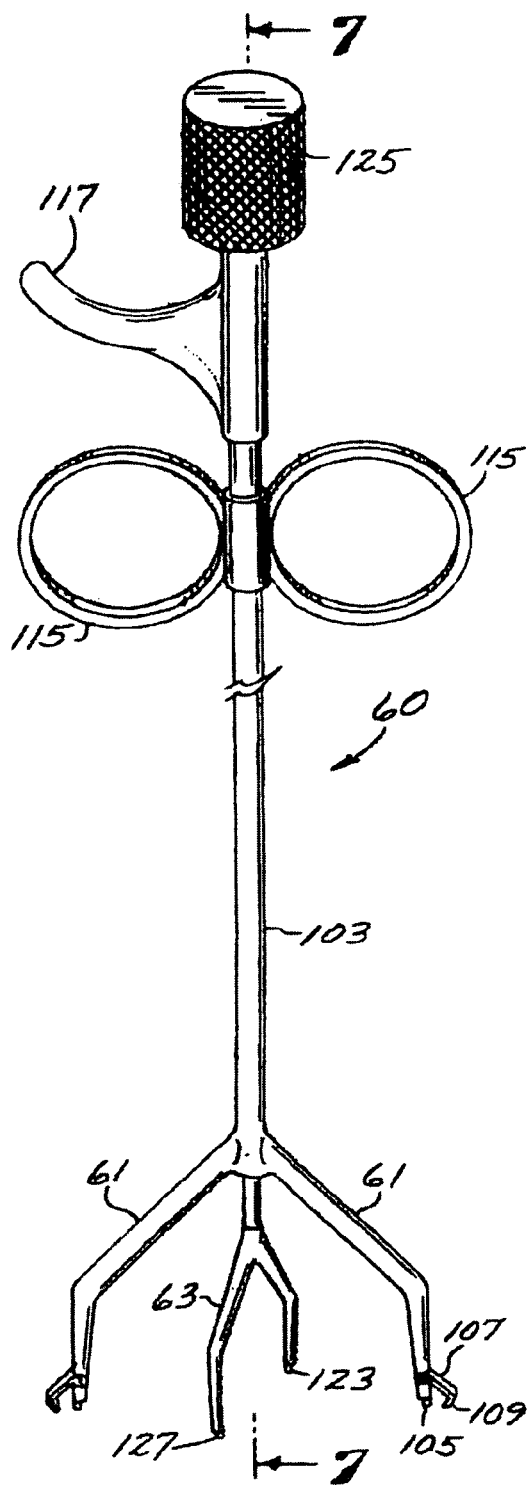
FIG. 5 is a broken perspective view of a deployment tool embodying the present invention.
Figure 6:
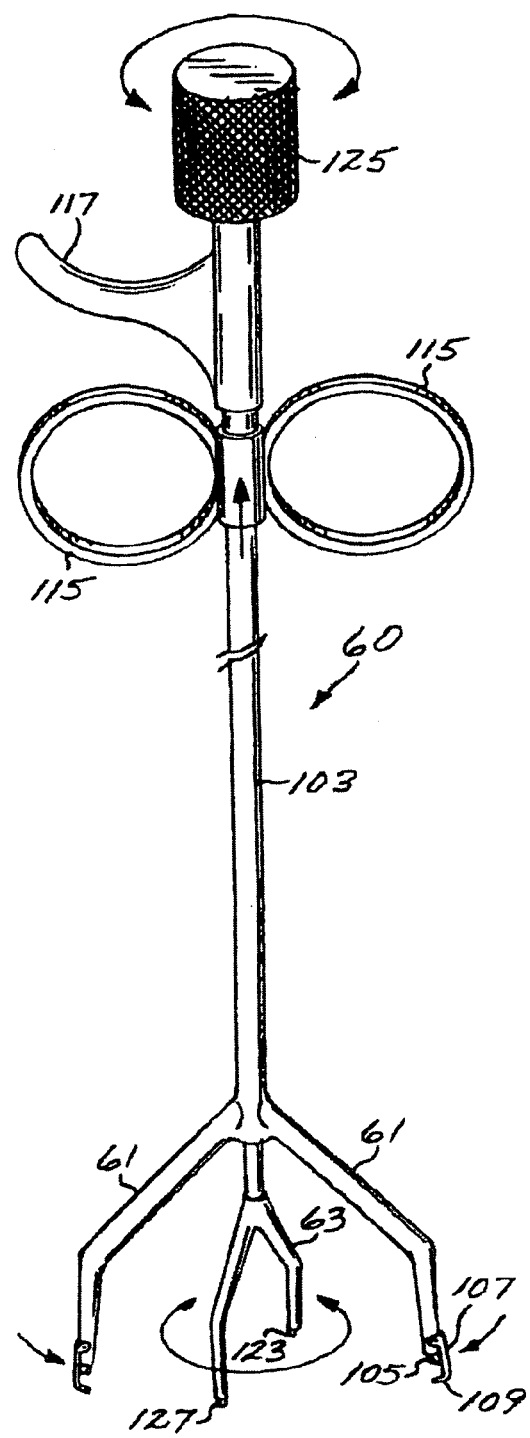
FIG. 6 is perspective view, similar to FIG. 5, but showing the employment tool manipulated.
Figure 7:
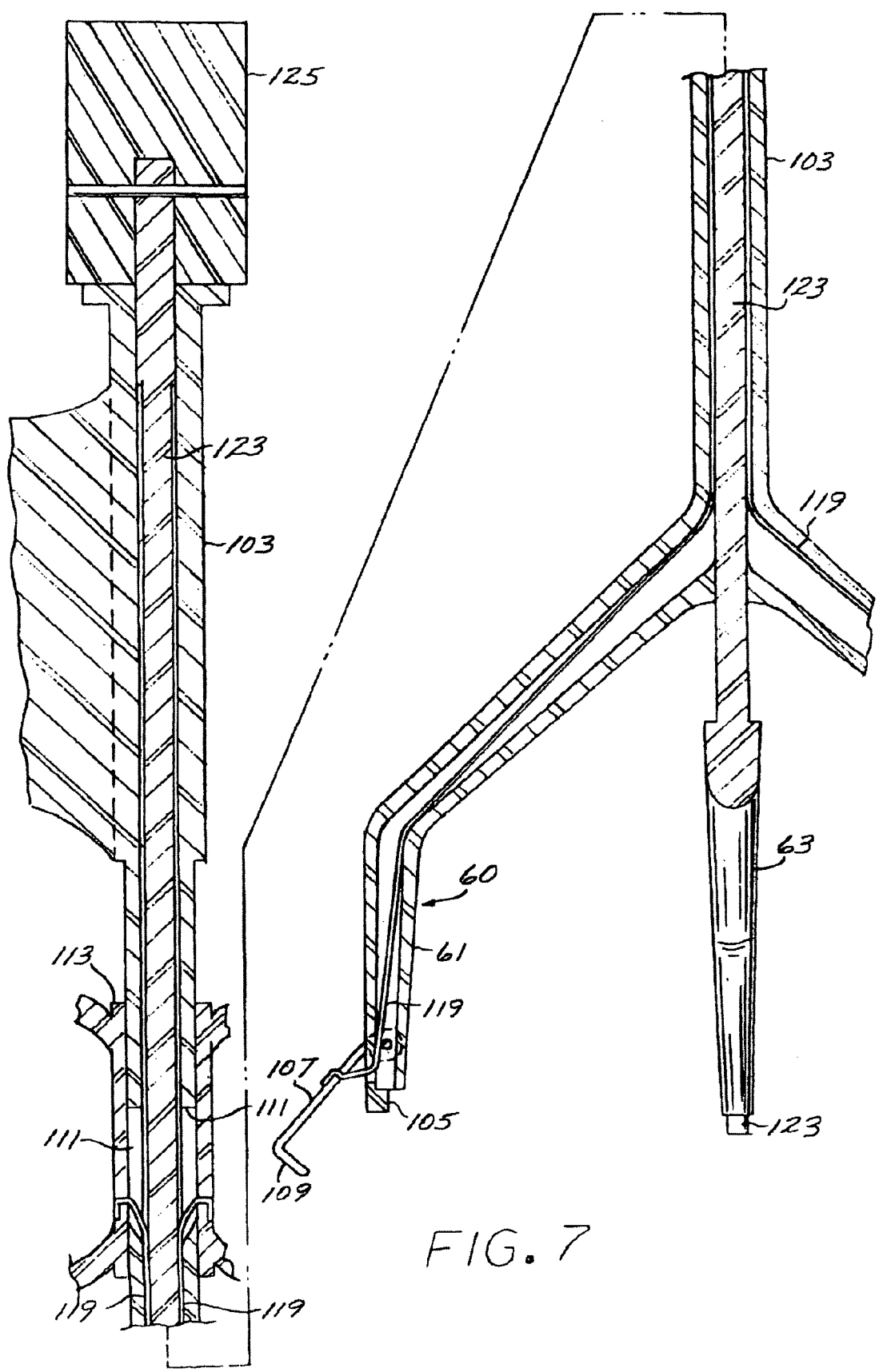
FIG. 7 is a longitudinal sectional view, in enlarged scale, taken along the line 7—7 of FIG. 5.
Figure 8:
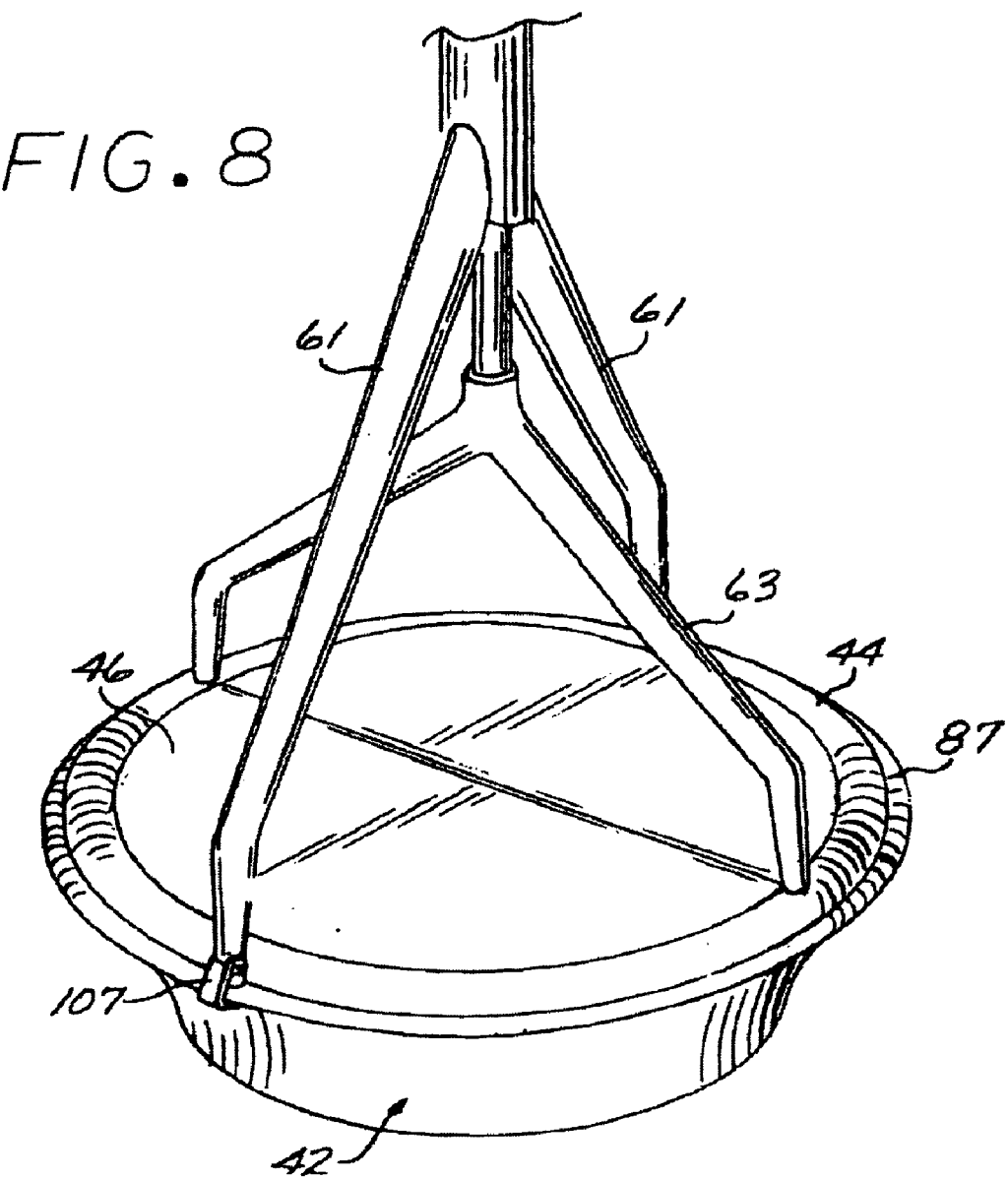
FIG. 8 is a perspective view showing the anchor device depicted in FIG. 1 engaged with the tool shown in FIG. 5.

Referring to FIGS. 5–7, the deployment tool 60 includes a longitudinally elongated housing tube 103 bifurcated at its distal extremity to form radially outwardly projecting tubular legs 61 configured at their radial distal ends with drive pins 105 for selective engagement with the bores 89 of the anchor (FIG. 2). Pivotally mounted at the distal extremities of such legs 61 adjacent such pins 105 are respective L-shaped pivotal claws 107 configured at their distal ends with respective laterally extending holding latches 109. The tube 103 is formed intermediately with a pair of diametrically oppositely disposed longitudinal slots 111 (FIG. 7) about which are telescoped a sleeve 113 mounting a pair of diametrically opposed release finger rings 115. Connected between the sleeve 113 and an intermediate location on the respective claws 107 are respective small push-pull wires 119 (FIG. 7) so that, when the rings 115 are retracted upwardly, the claws 107 are drawn downwardly to their latching positions shown in FIGS. 2 and 6.

Longitudinally telescoped through the housing tube 103 is a push-pull wire 123 which mounts at its proximal end a knurled knob 125 and is formed on its distal extremity with the respective tines 63, such tines being formed at their distal extremities with respective pegs 123 for receipt in the respective bores 93 (FIG. 2).

Mounted proximally on the housing tube 103 is a trigger fitting, generally designated 117, for engagement with the surgeon's thumb when the fingers are received in the rings 115. This trigger fitting permits stabilization and optimal hand comfort for the surgeon when using the deployment tool 60.

The housing tube is constructed from a relatively rigid material such as plastic or titanium but could also be formed from stainless steel. The housing tube should be of sufficient length so as to allow easy and convenient access to the patient's heart from outside the chest cavity. In the preferred embodiment, the housing tube has a length of 30 cm for optimal access to the thorax but such length is not to be limiting since a shorter length may be appropriate for the pediatric procedure while a longer housing tube may be better suited for larger patients.

In operation, to perform a heart valve replacement surgery, access is gained to the heart by making a small incision at one of several locations such as the superstenal notch passing below or though the manubrium or sternum or via a mini-thoracotomy incision in the area between the first and second ribs enabling visualization of the aorta. A second parallel incision may be made for insertion of a trocar tube and placement therein of a monoscopic endoscope, coupled with a monitor, for optimal viewing of the valve site during the procedure. A hole is then made in the pericardium of the heart and the patient is placed on cardiopulmonary bypass using either a peripheral or central cannulation. At the surgeon's option, the aorta may then be cross-clamped and arrested using any of the usual techniques. A heart venting device can then be inserted and a small incision in a heart or great vessel above the annulus is made so the valve can be excised. Once this is accomplished the annulus is debrided as required. The anchor 39 will have been pre-fitted in its valve socket 88 formed with a universal mounter for use with any of the commercially available mechanical or tissue prosthetic valves (FIG. 2). The anchor 39, with prosthetic valve in place, is then ready for attachment with the deployment tool 60.

Figure 9:
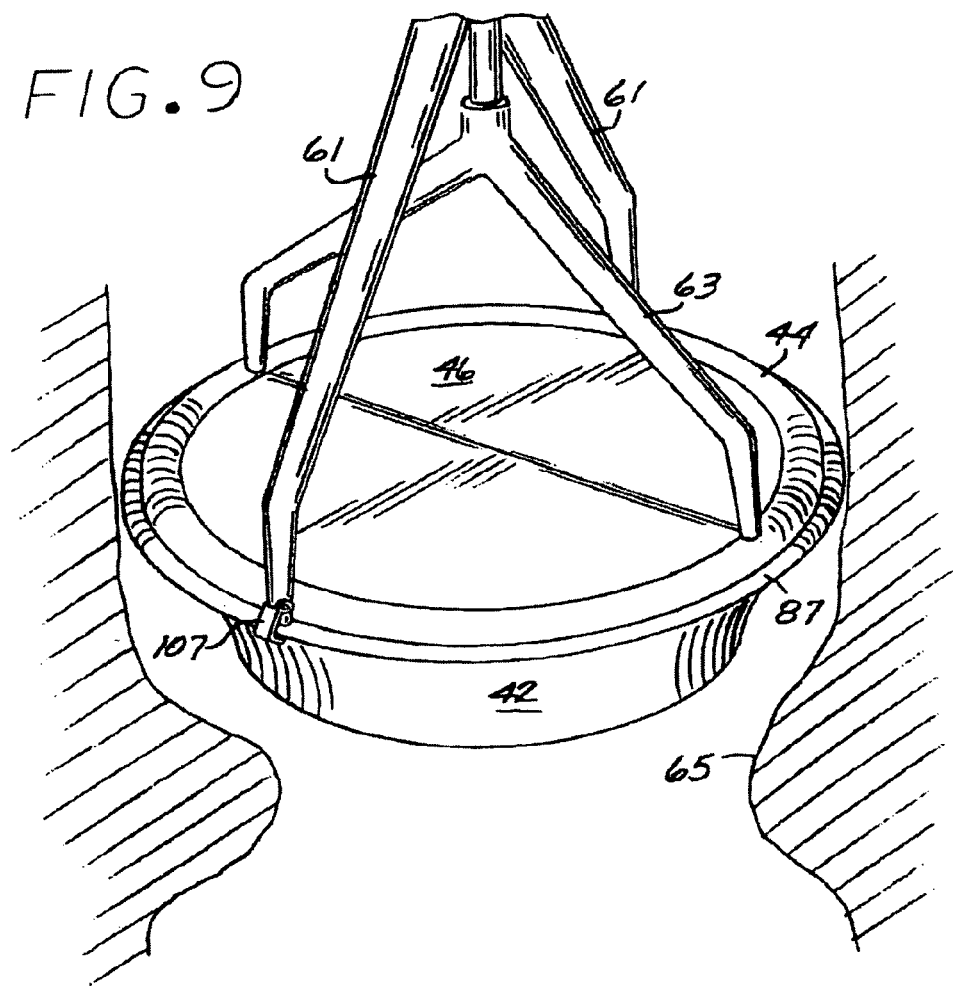
FIG. 9 is a view similar to FIG. 8 but showing the anchor device being inserted in a native annulus.

The anchor device 39 is then mounted to the distal extremity of the deployment tool 60 by inserting the pegs 127 of the tines 63 in the bores 93 and engaging the pegs 105 in the bores 89. The surgeon may then grasp the actuating rings 115 and shift them proximally toward the trigger 117 to thus draw the respective claws 107 downwardly inwardly, as viewed in FIG. 7, to thus draw the respective latches 109 under the flange 87 to latch such tool to the anchor device (FIG. 2). The latches 109 function as a stabilizing device to secure the tool 60 attached to the anchoring device 39 and prosthetic valve may then be inserted through the thoracic incision and advanced to position such anchor device in the optimal location along the heart valve annulus and nested at the shelf 65, as shown in FIG. 9. Optimal placement of the device 39 will locate the radially out-turned flange 87 such that it will nest on top of the annular shelf 65 acting as a stop ring to prevent further insertion. With the anchor device 39 so positioned, the actuating knob 125 may rotate in one direction to screw the outer ring 42 upwardly relative to the inner ring 44 until it reaches the position shown in FIG. 3 engaging the outer tube flare with the inner flare stops 86. At this point, the retainer extremity 50 at the bottom of the outer ring 42 will clear the resilient retainer fingers 49 thus releasing the free ends of such fingers to spring radially outwardly to the respective position shown in FIG. 10 and engaging under the shelf of the annulus 65. This will then serve to secure the anchor device 39 firmly and atraumatically in position in such annulus.

The surgeon can then grasp the actuating rings 115 (FIG. 5) and pull upwardly thereby driving the sleeve 113 distally to thus shift the push-pull wires 119 driving the claws 107 upwards, as shown in FIG. 7, to release the respective latches 109 from under the ledge 87 (FIG. 2). This then will free the tool 60 to be withdrawn. The aortotomy may then be closed using traditional suturing technique or vascular staples. The heart can then be de-aired and the crossclamp removed. If an endoscope is utilized for viewing purposes, removal of the corresponding trocar tubes and endoscope may be effected. The patient is now ready to be removed from cardiopulmonary bypass. Once the patient is off bypass, the exterior wound may be closed and sutured using traditional technique.

It will be appreciated that the retainer fingers 49 are constructed from a flexible yet resilient metal or plastic material which is capable of being collapsed when withdrawn into the anchor before deployment and then released to its opened position upon deployment of the anchor device. Such a material may possess a spring-like quality or other sense memory so as to provide an added tension quality for enhanced security and tension against the annulus shelf when deployed. In the preferred embodiment, when fully deployed, the retainer fingers include a bent portion having a curved outer radius 51. This curved portion 51 enhances the surface area of the retainer fingers 49 in contact with the annulus shelf 65, thereby augmenting the gripping capabilities of the retainers. It can be appreciated that the shape and structure of the retainers can vary widely. The retainers may in fact take a variety of forms including that of a resilient retractable spring-like finger 317 (FIG. 22) which projects radially outwardly and upwardly to cup under the shelf of the annulus and thereby secure the anchor in place. Alternatively, the retainer fingers need not project from the distal end of the anchor. In one proposal, the retainer fingers may project and retract from axial windows which are formed about the periphery of the anchor device.

Figure 4:
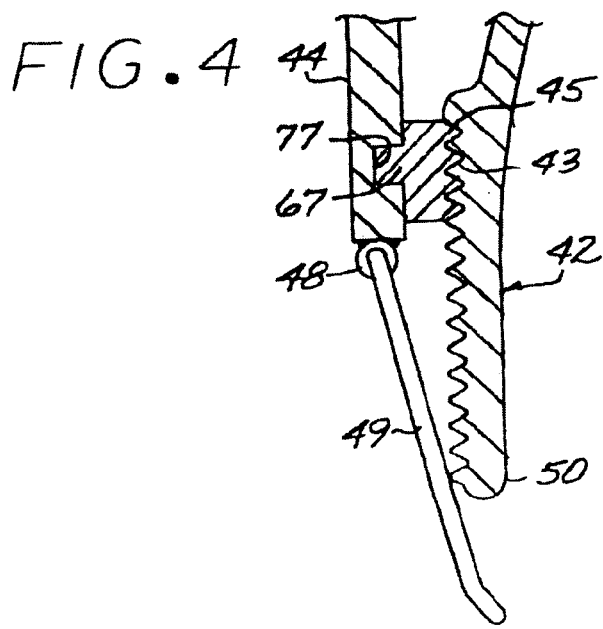
FIG. 4 is a sectional view, in enlarged scale, showing the anchor driver device in a retracted position.

It will be appreciated that, in the event the prosthetic valve device mounted by the anchor device of the present invention should fail the heart valve may be reaccessed as set forth above and the valve occluder 46 removed leaving the anchor ring in place. Such anchor may then be cleaned up and the occluder replaced. In addition, should it be necessary to remove the anchor, a tool like that described hereinabove may be used to withdraw the retainer elements 49 radially outwardly to clear the annulus for removal. The deployment tool 60 may then be actuated by grasping the knob 125 drawing it proximally to retract the tines 63. Concurrently, the rings 115 may be grasped and driven distally to drive the claws 107 counterclockwise as viewed in FIG. 7 to open such claws. The tool may be advanced to engage the prongs 105 with the flange 87. The housing tube 103 may then be rotated while holding such prongs 105 engaged against such flange 87 to thus register such prongs with the bores 89. It will be appreciated that in some embodiments of the present invention an upwardly opening groove is formed about the flange 87 on the diameter including the bores 89 to guide such prongs 105 as they are orbited about to locate such bores. Once such prongs 105 are engaged, the latch rings 115 may be advanced distally to rotate the claws 107 to latch under such flange 87. The knob 125 may then be grasped and advanced distally while holding the housing tube 103 stationary. Once the tine prongs 123 engage the inner ring flange 91, the knob 125 may be rotated until such prongs 123 engage the bores 93. The knob 125 may then be advanced to engage such prongs firmly in the bores 93 and the tool components held steadily as the knob is rotated to advance the screw thread actuator 67 thereby moving the outer ring 42 downwardly so as to advance such retainers radially inwardly to engage the bottom end of the retainer skirt 50 medially with the free ends thereof to clear the underside of the annulus (FIG. 4) while holding the latch rings proximally to hold the latches 109 secure on the flange and the surgeon may grasp the housing tube 103 and draw it proximally to remove the anchor.

Figure 11:
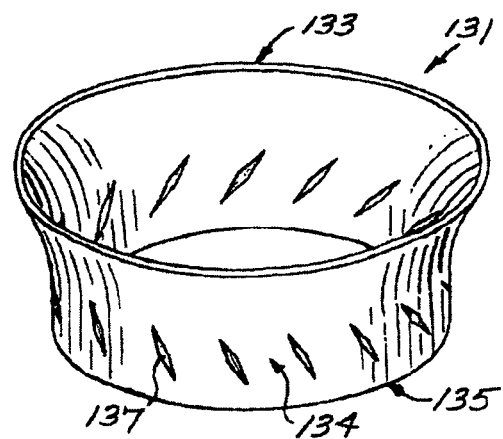
FIG. 11 is a perspective view of a second embodiment of the prosthetic valve anchor apparatus of the present invention.
Figure 12:
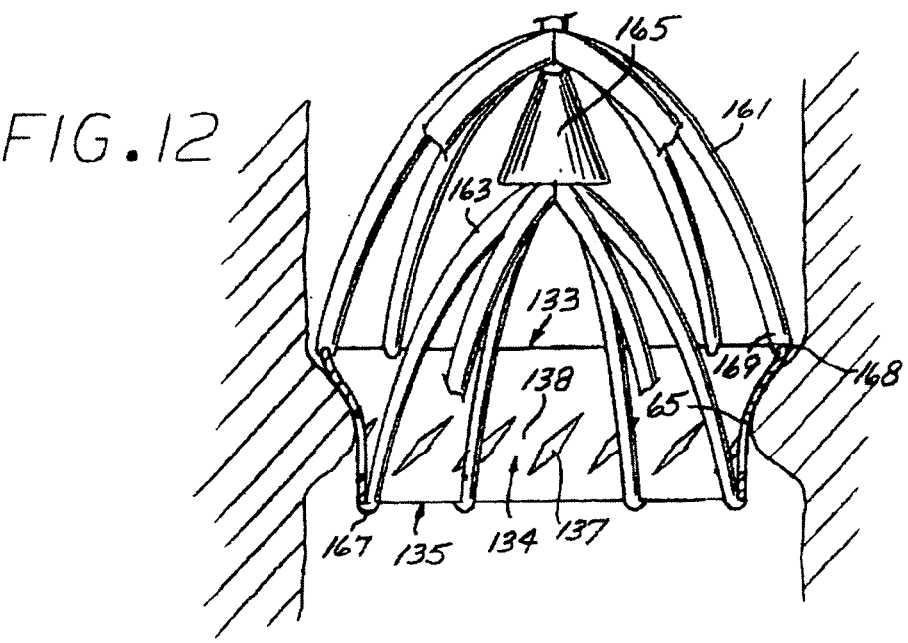
FIG. 12 is a perspective view, partially in section, of the anchor device shown in FIG. 11 being inserted in an annulus.
Figure 13:
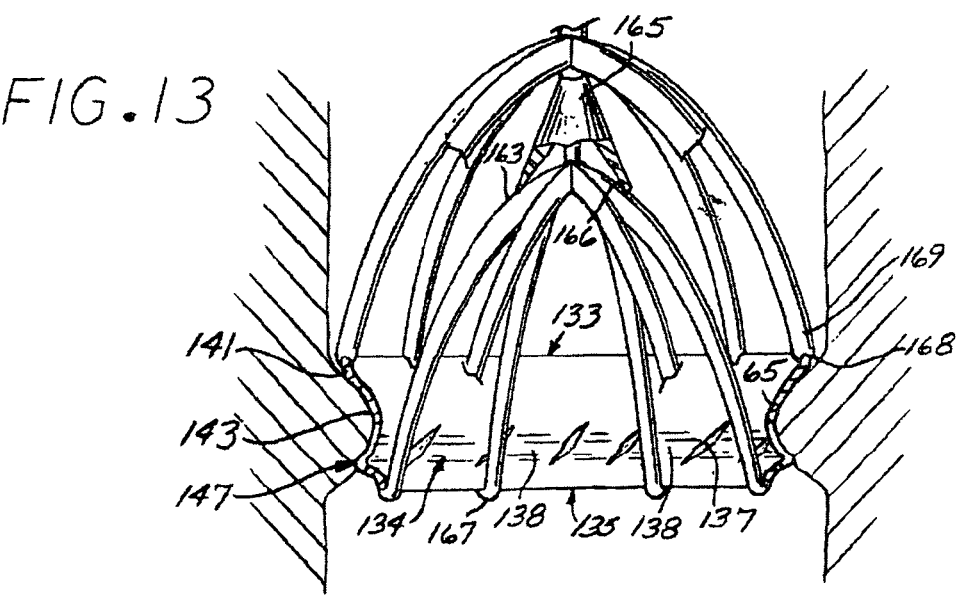
FIG. 13 is a side view similar to FIG. 12 but showing the retaining device as being deployed.

Referring to FIGS. 11 through 13, a second embodiment of the anchor apparatus of the present invention, shown without the prosthetic valve in place, includes, generally, a ring forming a band 131 having upper and lower ring elements 133 and 135. Interposed between the upper and lower ring elements 133 and 135 is an actuating ring, generally designated 134, configured with diamond shaped fold-inducing openings 137 spaced peripherally thereabout and configured and arranged to form therebetween axial panels 138 having their respective narrowest annular dimension on a circumferential line positioned to be, when the band is compressed axially splayed radially outwardly under the annulus shelf (FIG. 13) to cooperate in defining a retainer ring, generally designated 147. The ring may be constructed of a stressed metal covered with a biocompatible substance, or a semi-rigid plastic capable of a spring memory so that upon deployment, the anchor device will retain the axially shifted configuration without additional support.

The ring is so configured and so shaped that, when axially compressive forces are applied thereto, it will assume the modified hourglass shape shown in FIG. 13. The actuating ring 134 may include a variety of constructions to achieve the necessary preferential bending. In one instance, the materials may be pre-stressed to achieve the desired form; in another example, the actuating ring may comprise a weakened area which will partially collapse upon axial column loading while operating to drive the retainer ring section 147 radially outwardly under the annulus.

Figures 14, 15:
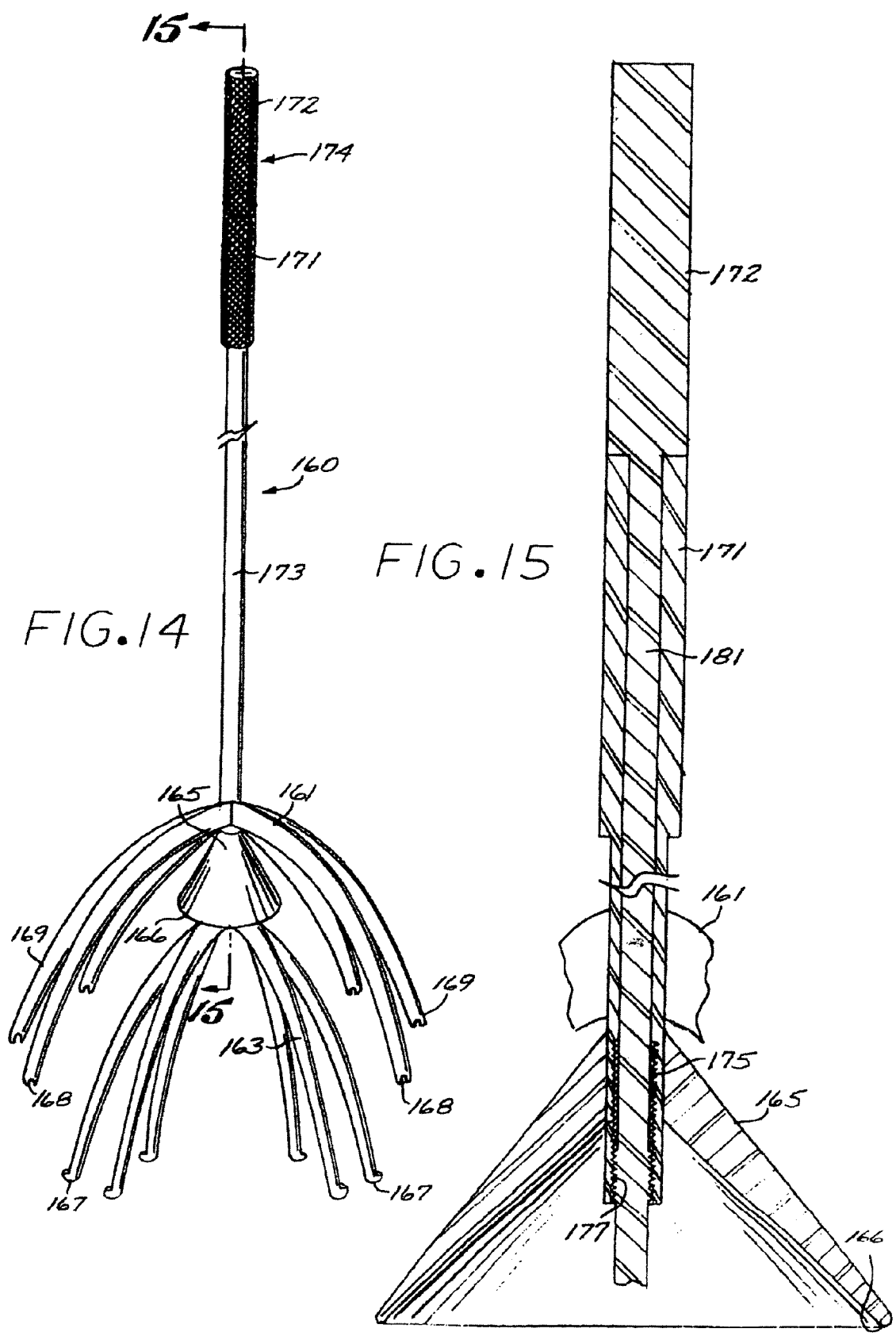
FIG. 14 is a broken perspective view of the tool utilized to deploy the anchor device shown in FIGS. 12 and 13.
FIG. 15 is a partial broken vertical sectional view, in enlarged scale, taken along the line 15—15 of FIG. 14.

Referring to FIGS. 14 and 15, the second embodiment of the deployment tool, generally designated 160, includes an elongated housing tube 173 formed on its distal end with radially outwardly and distally projecting legs 161 formed at their radial distal ends with pusher forks 169 formed with inverted U-shaped pairs of tines168 for engagement with the upper ring element 133 (FIG. 12). The deployment tool 160 is formed on the distal end of the housing tube 173 with a concentric, downwardly opening hollow retractor cone 165 terminating in a retractor edge 166.

The housing tube 173 houses an interior actuator wire 181 capable of longitudinally telescopic axial movement within the housing 173. The actuator wire 181 is formed distally with a plurality of external screw threads 177 screwably engaged with oppositely placed internal screw threads 175 formed in the distal end of the housing tube 173. Formed at the distal extremity of the actuator tube 181 are radially outwardly and distally projecting resilient legs 163 formed at their distal ends with respective radially out-turned L-shaped engagement hooks 167. Such legs 163 are formed with an inherent bias to push such hooks radially outwardly into a circular pattern having a diameter slightly larger than the diameter of the distal ring section 135 (FIG. 13). The engagement hooks 167 are configured to securely grasp and engage the distal edge of the ring 135. The proximal extremity of the tubular housing 171 is formed with an enlarged-in-diameter knurled tubular handle 171 having abutted against the proximal end thereof the distal shoulder of an enlarged-in-diameter cylindrical handle formed at the proximal end of the wire 181.

In operation, the deployment tool 160 may be attached to the anchor 131 device by advancing the wire 181 to shift the legs 163 distally. The legs 163 may be pressed radially inward by hand to allow the ring anchor 133 to be fitted thereover to be moved proximally of the hooks 167. Such legs may be then released to engage such hooks with the distal edge of the ring section 135 (FIG. 12). Concurrently, the forks 168 may be engaged over the proximal edge of the ring section 133. Access will be gained to the anatomy as described above. The tool carrying such anchor is then inserted into the patient using the surgical technique described hereinabove to be located at the annulus shelf site. When the anchor has been placed in the desired location, the activating handle 172 may be grasped and rotated while holding the housing handle 171 to rotate the mating threads 177 and draw the wire 181 proximally to retract upwardly to draw the engaging hooks 167 proximally relative to the forks 169 to apply column loading to the ring 131. The application of such compressive force will cause the central actuator ring 134 to assume its preferential orientation driving the axially central parts of the panels 138 radially outwardly to form the retainer ring 147 (FIG. 13). Such panels 138 will thus exceed their tensile strength thus becoming overstressed to cause the anchor 131 to be retained in the hourglass shape of FIG. 13 with the retainer ring 147 pushed radially outwardly under the shelf of the annulus 65. At the maximum position of radial projection of the ring 131, the legs 163 will have been drawn proximally to the point at which they abut against the bottom edge portion 166 of the retractor cone 165. Thereafter, the surgeon can continue to rotate the upper knob 172 to draw the wire 181 further proximally to draw the proximal roots of the collapsible legs 163 further proximally and into such cone so as to flex such legs radially inwardly and disengage the hooks 167 from the bottom portion of the ring 135. The deployment tool may then be removed from the patient. The patient may then be taken off bypass, have the surgical openings closed and the procedure completed.

Should the occasion arise where the prosthetic valve shown in FIG. 11 is to be removed or replaced, a tool like that described above may be employed to retract the anchor ring 131 and remove the device from the annulus shelf. Such a tool will employ legs and tines like those shown except with clamps on the distal extremities thereof for grasping the respective top and bottom of the ring 131. The heart valve must first be reaccessed using the surgical techniques previously described herein. Thereafter the deployment tool 160 may be used by first retracting the legs 163 to their fully retracted position within the cone 165 so that the tool may be inserted into the patient and placed such that the clamps in the respective forks 169 and tines 168 are in engagement with the respective top and bottom ends of the ring 131. The upper knob 172 may then be rotated to actuate the screw threads so as to drive the wire 181 distally to apply tensile forces to the ring 131 causing it to straighten to the position shown in FIG. 11 with the retainer ring drawn radially inwardly to clear the annulus 65 as such tool is drawn proximally to remove the ring 131.

Figure 16:
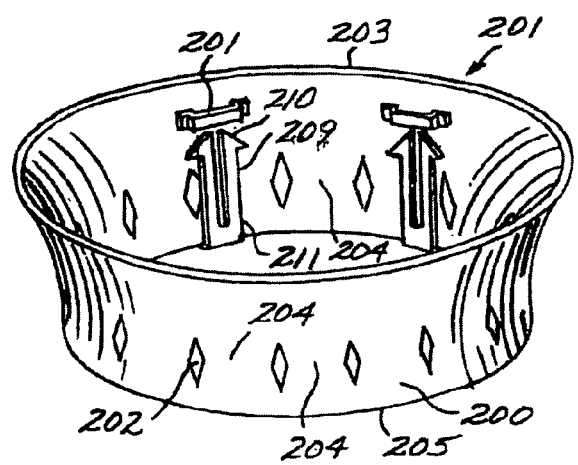
FIG. 16 is a perspective view of a third embodiment of the anchor device of the present invention.
Figure 17:
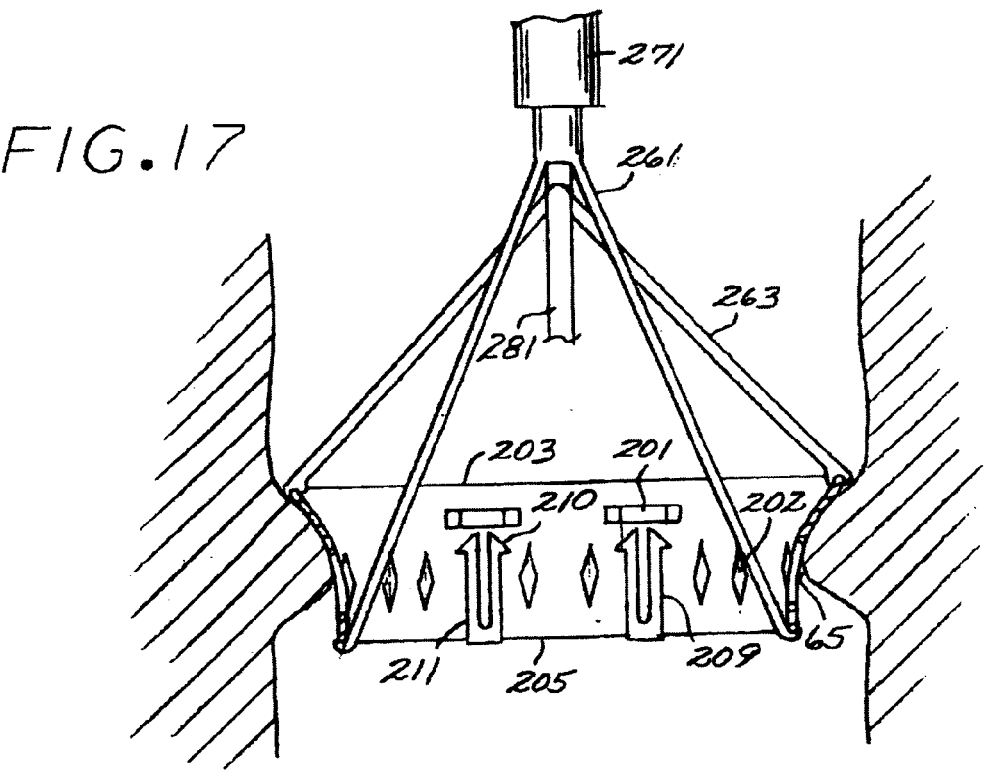
FIG. 17 is a transverse sectional view of the anchor device shown in FIG. 16 being deployed by a deployment tool in a native annulus.
Figure 18:
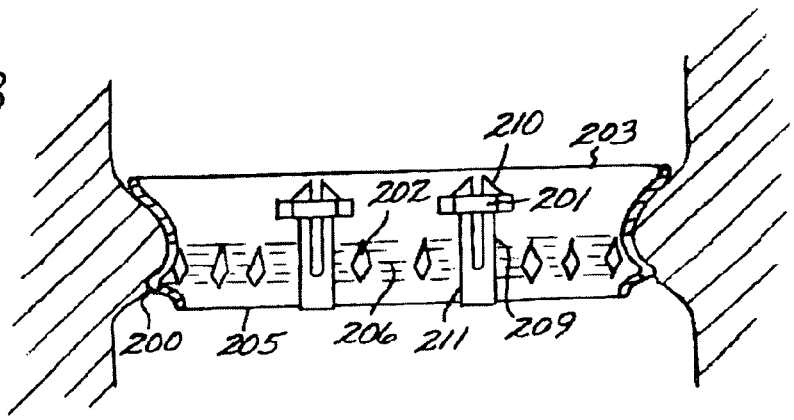
FIG. 18 is a sectional view showing the anchor device of FIGS. 16 and 17 retained in the annulus.

The third embodiment of the prosthetic valve anchoring device of the present invention shown in FIGS. 16–18 without the prosthetic valve in place, includes a band, generally designated 201, somewhat similar to that shown in FIG. 11. The band 201 is formed with proximal and distal ring elements 203 and 205, respectively, and an actuator ring element 204 interposed between the proximal and distal elements. The distal ring element 205 is constructed with a retainer ring element, generally designated 200, having diamond shaped cut outs 202 spaced annularly apart to form said bands 206 which, when axial forces are applied, will splay radially outwardly to assume a diameter larger than that of the annulus to form an enlarged-in-diameter retainer.

Mounted about the interior of the proximal band element 203 are a plurality of rectangular latch brackets 207 configured with longitudinal passages. Corresponding elongated resilient latches, generally designated 211, are cantileverly mounted on the distal band element 205 and are bifurcated to form tines 209 configured on their respective free ends with modified arrowhead shaped catch teeth 210. Thus, when the axially compressive forces are applied to the anchor band 201 to axially compress such band, such latches will be driven toward the respective passages in the brackets 207 to engage the catch teeth 210 of the respective tines 209 with the circumferentially opposite ends of such bracket to be flexed therein laterally inwardly toward one another until they clear the respective brackets 207. The tines will then snap laterally outwardly to cause the catch teeth 210 to latch in the position shown in FIG. 18 to lock against release.

Referring to FIGS. 19 and 20, the third embodiment of the deployment tool, generally designated 260, includes an elongated tubular housing 271 formed on its proximal end with a hand grasp knob 273 reduced in diameter centrally to form a waist. Such housing terminates at its distal end in a retractor edge 276 (FIG. 20) which may be conically shaped. Telescoped through such housing 271 is an intermediate actuator tube 275 having mounted at its proximal end a pair of trigger loops 215 (FIG. 19). These trigger loops 215 also comfortably stabilize the surgeon's hands when using the deployment tool in a manner similar to the trigger fitting shown in FIGS. 5 and 6. Formed on the distal end of the actuator tube 275 are radially outwardly distally projecting resilient legs 261 configured at their radial distal ends with respective L-shaped proximally facing hooks 267. Referring to FIG. 20, such legs are so positioned that, upon retraction of the actuator tube 275, they will engage the retractor edge 276 to be drawn radially inwardly. The L-shaped hooks 267 are configured to engage under the distal edge of the band 205 for deployment of the anchor 201. Formed at the distal end of the actuating wire 281 are radially outwardly and distally projecting legs 263 configured at their distal ends with pusher forks 269 having inverted U-shaped tines 268 for secure nesting with the proximal edge of proximal ring element 203 (FIG. 16). The surgeon may then pull the ring 217 proximally to retract the actuating wire 281 proximally causing the hooks 267 to move proximally thereby exerting column load on the band thereby compressing the band 201 axially as described above causing the latch forks 211 to be driven into the respective passages of latch brackets 207 thereby securing the anchor 201 in such deployed position, as shown in FIG. 18.

As the anchor band 201 approaches full deployment, the anchor ring 201 will be sufficiently crushed axially so the tube 275 will be drawn sufficiently far proximally in the tube 275 to cause the roots of the legs 261 to engage the retractor edge 276 (FIG. 20) to drive such legs radially inwardly to disengage the respective hooks from the distal edge of the ring element 205 (FIG. 18). The tool may then be removed.

Figure 21:
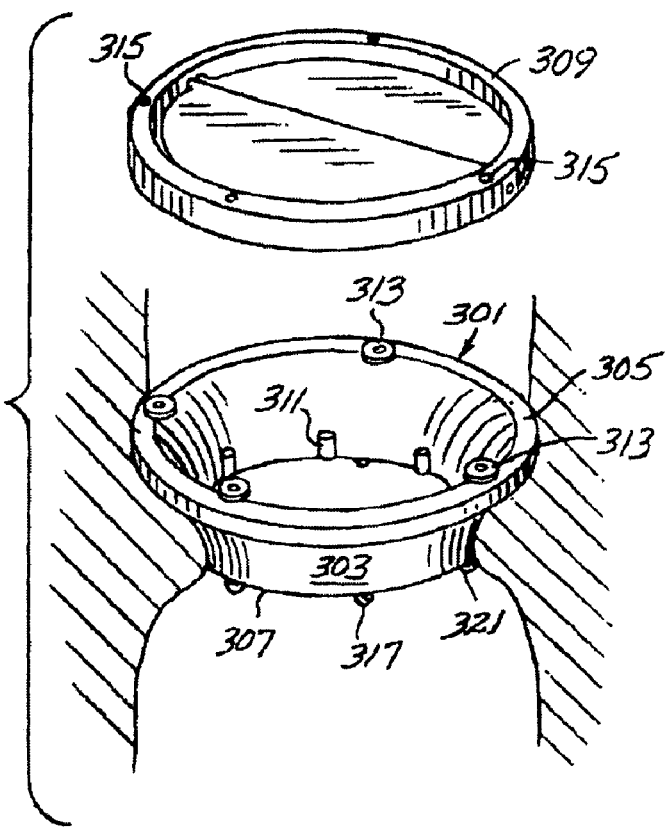
FIG. 21 is a perspective view, of a fourth embodiment of the prosthetic valve anchor apparatus of the present invention, showing the anchor device being inserted into a native annulus.
Figure 22:
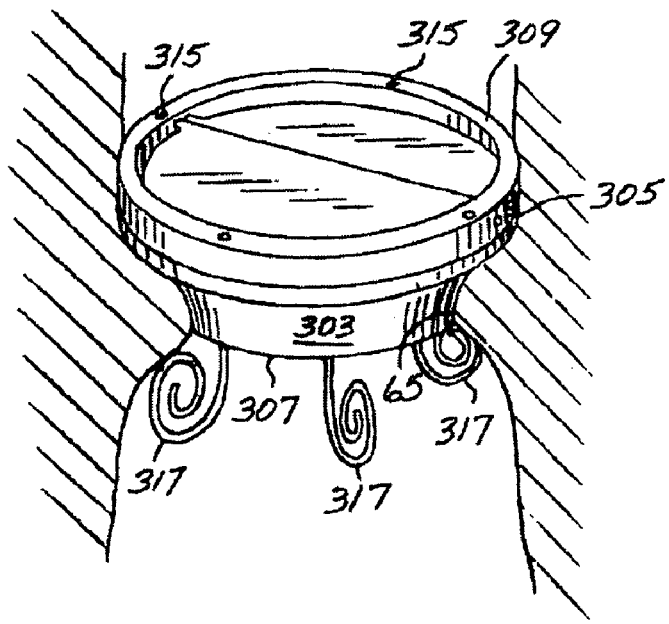
FIG. 22 is a view similar to FIG. 21 but showing the retaining device as being deployed.

The embodiment of the prosthetic anchor device 301 shown in FIGS. 21 and 22 is similar to the construction shown in FIG. 1. Here, generally, the anchor device 301 includes a bell shaped ring 305 having annularly spaced apart inner and outer walls to be configured with a downwardly opening annulus which receives axially therein a plurality of vertically projecting formed retainer springs 317 which may be configured on their lower extremities with light coil springs. Such retainer springs 317 are deployed vertically downwardly to take their inherent set projecting radially outwardly to engage under the shelf of the annulus 65 below the minor diameter thereof.

Any one of a number of different deployment actuation devices may be utilized to deploy such retainer rings 317. One such mechanism may be like that shown in FIG. 21 where formed tubular elements 313 are configured in alignment with such springs 317 and are opened at the top end for longitudinal receipt of pusher tines which engage therewith and are advanced downwardly axially to push against the top ends of the respective springs 317. In this configuration, it will be appreciated that the mounting ring 309 of the prosthetic is itself formed with bores 315 configured to be aligned with the bores 313.

In another modification, the actuating mechanism is in the form of inner and outer bell shaped rings spaced apart to form an annulus and rotatable relative to one another about their central axes. In that configuration, the top extremities of the respective retainer springs 317 are anchored to one of the rings and passes medially over a pair of close spaced, radially projecting pegs and downwardly through vertical tubes defining passages so that, as one ring is rotated relative to the other, such springs 317 are either advanced downwardly in the respective tubes for deployment or are retracted upwardly in the respective tubes for retraction. In either of these configurations, relative rotation of the two rings may be established by a deployment tool similar to the device shown in FIGS. 5 and 6. In a further modification, such retainer springs are telescopically received in open ended stub tubes 311 mounted around the interior of the ring 305 and are advanced outwardly therethrough by relative rotation of a complementally shaped inner actuation ring (not shown) to which the top ends thereof are tethered for advancement and retraction as such inner end is rotated in opposite directions.

It will be appreciated that the method of placement and retaining of the heart valve anchor utilizing the present invention will facilitate stabilization of the anchor at the annulus during the delicate placement portion of the surgery to achieve reduced trauma to the patient, as well as offering secure retaining of the device after deployment using less invasive technique. Furthermore, both the anchor device and deployment tool are manufactured using a minimal number of moving parts thereby eliminating altogether or reducing moving parts which may break or become misplaced prior to or during the surgery. Additionally, in some of the embodiments, the anchor device can be formed as a single unit thereby permitting the greatest strength possible in the overall apparatus.

From the foregoing, it will be appreciated that the anchor device of the present invention is economical to manufacture and can be inserted using minimally invasive surgical procedures in a relatively rapid manner without the usual tedious and time consuming tasks typically associated with suturing. The device provides for secure and positive anchoring in the native annulus and possesses the characteristics that the procedure might be reversed to remove the anchor device for replacement of the occulators.

Various modifications and changes may be made with regard to the foregoing detailed description without departing from the spirit of the invention.

What is claimed is:

1. A method for implanting a heart valve anchor in a heart annulus comprising the steps of:
    selecting an anchor device for receipt through said annulus including spaced apart ring elements shiftable axially relative to one another from recessed to deployed positions and a retainer retained between said ring elements operable upon said ring elements being shifted from a retainer recessed position to a retainer deployed position projecting radially outwardly;
    accessing an artery of said patient and inserting said anchor device therethrough to position it in said annulus; and
    shifting said ring elements axially relative to one another to said deployed position by rotating them relative to one another to shift said retainer to said retainer deployed position.

2. A method for implanting a heart valve anchor in a heart annulus comprising the steps of:
    selecting an anchor device for receipt through said annulus including spaced apart ring elements threaded to one another and shiftable axially relative to one another from recessed to deployed positions and a retainer retained between said ring elements operable upon said ring elements being shifted from a retainer recessed position to a retainer deployed position projecting radially outwardly;
    accessing an artery of said patient and inserting said anchor device therethrough to position it in said annulus; and
    shifting said ring elements axially relative to one another to said deployed position by rotating said ring elements relative to one another to shift them axially relative to one another to shift said retainer to said retainer deployed position.

3. The method for implanting a heart valve anchor as set forth in claim 1 or 2, wherein:
    said step of selecting said anchor device includes selecting said anchor device to include a radially outwardly projecting stop ring on a proximal end thereof, and
    said step of inserting said anchor device includes inserting it sufficiently far to position said stop ring on a proximal side of said annulus.

4. The method for implanting a heart valve anchor as set forth in claim 1 or 2, that further includes the steps of:
    after shifting said retainer to said retainer deployed position, shifting said ring elements to said recessed position to shift said retainer from said retainer deployed position to said retainer recessed position.

5. The method for implanting a heart valve anchor as set forth in claim 1 or 2, that further includes the step of:
    imbedding said retainer in said annulus.

6. The method for implanting a heart valve anchor as set forth in claim 1 or 2, wherein:
    said step of inserting said device includes selecting an elongated introduction tool having a semi-rigid tubular tool housing and an elongated deployment rod projecting therethrough and coupling the distal end of said tool housing with one of said ring elements and the distal extremity of the other ring element with the other of said ring elements.

* * * * *

UNITED STATES PATENT AND TRADEMARK OFFICE
CERTIFICATE OF CORRECTION

PATENT NO. : 6,893,459 B1
DATED : May 17, 2005
INVENTOR(S) : John A. Macoviak

It is certified that error appears in the above-identified patent and that said Letters Patent is hereby corrected as shown below:

Title page,
Item [56], References Cited, U.S. PATENT DOCUMENTS, insert
-- 3,143,742 issued to Harry W. Cromie on 08/1964 --.

Signed and Sealed this

Twenty-third Day of August, 2005

JON W. DUDAS
*Director of the United States Patent and Trademark Office*